United States Patent [19]

Magnin et al.

[11] Patent Number: 5,103,036

[45] Date of Patent: Apr. 7, 1992

[54] PROCESS FOR PREPARING 3-ALKENYLIDENE-1,1-BISPHOSPHONATES

[75] Inventors: David R. Magnin, Hamilton; Richard B. Sulsky, Somerville, both of N.J.

[73] Assignee: E. R. Squibb & Sons, Inc., Princeton, N.J.

[21] Appl. No.: 699,047

[22] Filed: May 13, 1991

[51] Int. Cl.$^5$ ............................................. C07F 9/40
[52] U.S. Cl. ............................................. 558/161
[58] Field of Search ................................... 558/161

[56] References Cited

PUBLICATIONS

Thompson, W., et al., Tetrahedron Letters, 1990, 31, 6819–6822.
Marshall, J., et al., J. Org. Chem., 1987, 52, 2378–2388.
Trost, B., Angew. Chem. Int. Ed. Eng., 1989, 28, 1173–1192.
Trost, B., et al., J. Am. Chem. Soc., 1979, 101, 1595–1597.

*Primary Examiner*—Mary C. Lee
*Assistant Examiner*—Michael G. Ambrose
*Attorney, Agent, or Firm*—Burton Rodney

[57] ABSTRACT

A process is provided for preparing a 3-alkenylidene-1,1-bisphosphonate which is an intermediate for preparing an inhibitor of the enzyme squalene synthetase which is useful as an inhibitor of cholesterol biosynthesis, or which bisphosphonate itself is useful as an inhibitor of cholesterol biosynthesis. The process involves the palladium catalyzed coupling of an allylic ester with a tetraester of a methylenebisphosphonate to form a 3-alkenylidene-1,1-bisphosphonate containing an alkene moiety located γ, δ to the phosphonates.

17 Claims, No Drawings

PROCESS FOR PREPARING 3-ALKENYLIDENE-1,1-BISPHOSPHONATES

FIELD OF THE INVENTION

The present invention relates to a process for preparing 3-alkenylidene-1,1-bisphosphonates, (wherein the alkene moiety is γ, δ to the phosphonates), which are intermediates for preparing squalene synthetase inhibitors useful as inhibitors of cholesterol biosynthesis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413-441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J. R.; Goldstein, J. L.; Brown, M. S. Proc. Nat. Acad. Sci. USA, 1979, 76, 5018-5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

The alkylations of allylic esters with other nucleophiles such as malonate esters, sulfonoacetate esters and methylenebissulfones, has been pioneered by Trost and others as follows:

1) Thompson, W.; Tucker, T.; Schwering, J.; Barnes, J., Tetrahedron Letters, 1990, 31, 6819-6822
2) Marshall, J.; Andrews, R.; Lebioda, L., J. Org. Chem., 1987, 52, 2378-2388
3) Trost, B., Angew. Chem. Int. Ed. Eng. 1989, 28, 1173-1192
4) Trost, B.; Verhoven, T., J. Am. Chem. Soc. 1979, 101, 1595-1597

DESCRIPTION OF THE INVENTION

In accordance with the present invention, a process is provided for preparing 3-alkenylidene-1,1-bisphosphonates which process includes the step of reacting an allylic ester of the structure

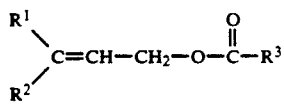

wherein $R^1$ and $R^2$ are the same or different and are H, alkyl, aryl or vinyl;
$R^3$ is alkyl, aryl, alkoxy or aryloxy; with a methylene bisphosphonate of the structure

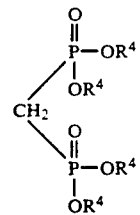

wherein $R^4$ is alkyl in the presence of a palladium catalyst, preferably $Pd[(C_6H_5)_3P]_4$, and an inert organic solvent, preferably tetrahydrofuran, optionally in the presence of a ligand such as triphenylphosphine, to form the 3-alkenylidene-1,1-bisphosphonates of the structures

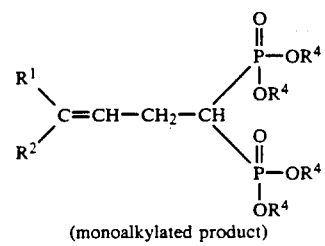

(monoalkylated product)

and

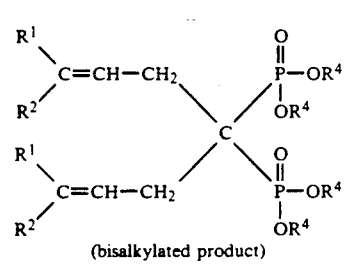

(bisalkylated product)

wherein the alkene moiety in each of bisphosphonates III and IV is located γ, δ to the phosphonates.

Where the above reaction is carried out in the presence of a proton scavenger, preferably bis(trimethylsilyl)acetamide (BSA), the monoalkylated product III is obtained in addition to a small percentage of the dialkylated product IV (less than 10%).

Conversely, where the above reaction is carried out in the presence of a base, preferably sodium hydride as a base, the dialkylated product IV is obtained as the major product and a small percentage of the monoalkylated product III (less than 10%) is obtained.

In an alternative embodiment of the process of the invention, monoalkylated products of the structure III are prepared by substituting allylic ester V

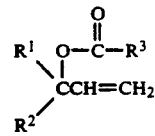

for the allylic ester I, employing the proton scavenger bis(trimethylsilyl)acetamide as described hereinbefore.

It has been found that when the relatively chemically stable allylic esters I and V are employed as substrates in the palladium catalyzed reaction in accordance with the present invention in place of highly reactive allylic halides (in the non-catalyzed reaction), higher yields of desired monoalkylated product III are obtained. For example, it has been found that when allylic halides are used as substrates in non-palladium catalyzed reactions, mixtures of monoalkylated product III and dialkylated product IV are obtained, and the desired monoalkylated product III is usually isolated in relatively low yield (30 to 50%). However, in accordance with the present invention, where a palladium-catalyzed alkylation using the proton scavenger BSA is employed, monoalkylated product III in yields that are generally greater than 60–70% are obtained.

The above reaction of the allylic compound I or V with methylene bisphosphonate II is carried out at a temperature of within the range of from about 25° to about 110° C., preferably from about 50° to about 90° C., under an inert atmosphere such as argon, for a period of from about 3 to about 48 hours, preferably from about 6 to about 24 hours.

The methylene bisphosphonate will be employed in a molar ratio to allylic compound I or V of within the range of from about 1:1 to about 5:1, preferably from about 1.5:1 to about 2.5:1.

The palladium catalyst will be employed in a molar ratio to allylic compound I or V of within the range of from about 0.01:1 to about 0.2:1, preferably from about 0.03:1 to about 0.1:1.

The ligand when present will be employed in a molar ratio to allylic compound I or V of within the range of from about 0.02:1 to about 0.4:1, and preferably from about 0.06:1 to about 0.2:1.

The proton scavenger will be employed in a molar ratio to allylic compound I or V of within the range of from about 1:1 to about 5:1, preferably from about 1.5:1 to about 2.5:1.

Examples of palladium catalysts suitable for use herein include, but are not limited to, tetrakis(triphenylphosphine)palladium, tetrakis(methyldiphenylphosphine)palladium, tris(dibenzylidene acetone)palladium, and bis(dibenzylidene acetone)palladium.

Examples of ligands suitable for use herein include, but are not limited to, triphenyl phosphine, tri-p-tolylphosphine, tri-o-tolylphosphine, 1,1'-bis(diphenylphosphino)ferrocene, 1,2-bis(diphenylphosphino)ethane, and 1,3-bis(diphenylphosphino)propane.

Examples of inert organic solvents suitable for use herein include, but are not limited to, tetrahydrofuran (THF), ethers, dioxane, toluene, benzene, dimethylformamide, dimethylsulfoxide and mixtures thereof.

Examples of proton scavengers suitable for use herein include, but are not limited to, bis(trimethylsilyl)acetamide, bis(trimethylsilyl)trifluoroacetamide, bis(trimethylsilyl)amine and triethylamine/chlorotrimethylsilane.

Examples of bases suitable for use herein include, but are not limited to, sodium hydride, potassium hydride, lithium hydride, sodium bis(trimethylsilyl)amide, potassium bis(trimethylsilyl)-amide, and n-butyllithium.

The starting allylic esters I and methylenebisphosphonates II are either known in the art or are prepared by procedures known in the art.

Examples of bisphosphonate starting materials II suitable for use herein include, but are not limited to, the following:

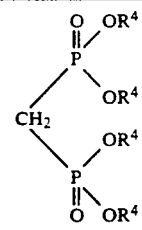

| $R^4$ |
|---|
| $CH_3$ |
| $C_2H_5$ |
| $C_4H_9$ |
| $C_5H_{11}$ |
| $CH(CH_3)_2$ |

Examples of allylic ester starting materials of the structure I or V suitable for use herein, are as follows

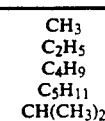

| $R^1$ | $R^2$ | $R^3$ |
|---|---|---|
| H | H | $C_6H_5$ |
| H | $CH_3$ | $CH_3$ |
| H | vinyl | $C_2H_5$ |
| $C_2H_5$ | $C_2H_5$ | $CH_3O$ |
| $C_3H_7$ | $CH_3$ | $CH_3$ |
| $C_6H_5$ | H | $CH_3$ |
| $C_6H_5$ | $CH_3$ | $CH_3O$ |
| vinyl | vinyl | $C_4H_9$ |
| $CH_3$ | $C_6H_5$ | $C_6H_5$ |

Further in accordance with the present invention, a method is provided for preparing the saturated analog of the monoalkylated product III having the structure VI

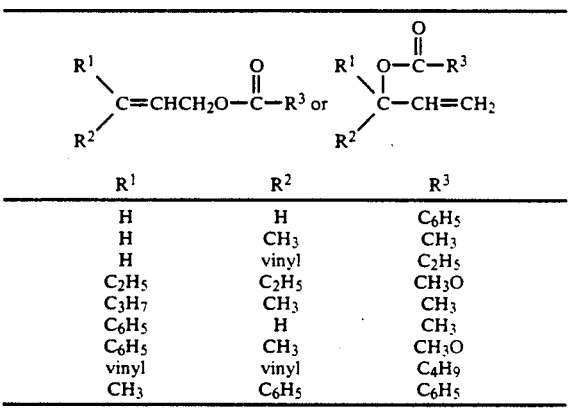

wherein the monoalkylated product III is hydrogenated, for example, by treatment with hydrogen in the presence of a palladium catalyst, such as Pd/C, to form VI.

Unless otherwise indicated, the term "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, (for example, F, Br, Cl or I or $CF_3$), alkoxy, aryl, arylalkyl, cycloalkyl, amino, hydroxy, alkylamido, alkanoylamino, alkanoylamido, arylcarbonylamino, nitro, cyano, thiol and/or alkylthio.

Unless otherwise indicated, the term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 to 4 substituents such as halo, alkyl, alkoxy, hydroxy, aryl, arylalkyl, cycloalkyl, alkylamido, alkanoylamino, arylcarbonylamino, amino, nitro, cyano, thiol and/or alkylthio.

Unless otherwise indicated, the term "aryl", "ar" or "Ar" as employed herein by itself or as part of another group refers to monocyclic or bicyclic aromatic groups containing from 6 to 10 carbons in the ring portion, such as phenyl, naphthyl or phenyl or naphthyl substituted with 1 to 3 substituents such as alkyl, halogen (Cl, Br or F or $CF_3$), alkoxy, hydroxy, amino, alkanoylamino, arylcarbonylamino, aryl, arylalkyl, cycloalkyl, alkylamido, nitro, cyano, thiol and/or alkylthio.

The terms "aralkyl", "aryl-alkyl" or "aryl-lower alkyl" as used herein alone or as part of another group refers to alkyl groups as discussed above having an aryl substituent, such as benzyl or phenethyl.

The terms "alkoxy", "aryloxy" or "aralkoxy" as employed herein alone or as part of another group includes any of the above alkyl, aralkyl or aryl groups linked to an oxygen atom.

The terms "alkylthio", "arylthio" or "aralkylthio" as employed herein alone or as part of another group includes any of the above alkyl, alkyl, aralkyl or aryl groups linked to a sulfur atom.

The terms "alkylamino", "arylamino", "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

The term "halogen" or "halo" as used herein refers to chlorine, bromine, fluorine, and iodine as well as $CF_3$, with chlorine or fluorine being preferred.

The term "amino" as used herein refers to unsubstituted amino as well as monosubstituted amino or disubstituted amino wherein the substituents may be alkyl and/or aryl.

The term "metal ion" refers to alkali metal ions such as sodium, potassium or lithium and alkaline earth metal ions such as magnesium and calcium.

The 3-alkenylidene-1,1-bisphosphonates III, IV and VI may be employed as intermediates in forming squalene synthetase inhibitors as disclosed in U.S. patent application Ser. No. 07/699,429 entitled "Bisphosphonate Squalene Synthetase Inhibitors and Method". In addition, the 3-alkenylidene-1,1-bisphosphonates III, IV and VI converted to their acid, or salt, or mixed ester-salts (as described in the above application) are synthetase inhibitors and thus may be used as inhibitors of cholesterol biosynthesis.

The compounds of Formulae III, IV and VI in their acid, salt or mixed ester-salt forms inhibit cholesterol biosynthesis by inhibition of de novo squalene production. These compounds inhibit the squalene synthetase enzyme and, in addition, some of these compounds inhibit other enzymes in the pathway from isopentenyl diphosphate to squalene, that is, farnesyl diphosphate synthetase and isopentenyl diphosphate-dimethylallyl diphosphate isomerase.

Thus, the above compounds are useful in treating atherosclerosis to inhibit progression of disease and in treating hyperlipidemia to inhibit development of atherosclerosis. In addition, the compounds of the invention may increase plasma high density lipoprotein cholesterol levels.

As bisphosphonates, the above compounds may also be useful in inhibiting formation of gallstones, treating tumors, lowering blood pressure, lowering blood sugar, treating diabetes mellitus, treating inflammation, as a diuretic, as an inotropic agent, as an antiarthritic (antirheumatic) agent, in treating other diseases of calcium and phosphate metabolism including treatment of bone resorption, Paget's disease, osteoporosis, calcification of joints, implants and metastasis, as antitartar and anticalculus agents in toothpastes and mouthwashes, treating various stones and calculi, treating sickle cell anemia, treating hypoxia and ischemic tissue, and as an antiameobal agent, as well as for use in complexes with technetium-99m and radioiodinated derivatives for use as diagnostics.

The above compounds may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG-CoA reductase inhibitors such as lovastatin, pravastatin, velostatin or simvastatin.

The above compounds to be employed in combination with the squalene synthetase inhibitor compounds will be used in amounts as indicated in the Physicians' Desk Reference (PDR).

The above compounds may also be employed with sodium lauryl sulfate or other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

Preparation of Rat Liver Microsomes

Livers are dissected from 2 or 3 decapitated Sprague Dawley rats and are quickly transferred to ice cold buffer (potassium phosphate, 0.05M, pH 7.4); $MgCl_2$, 0.004M; EDTA, 0.001M; and 2-mercaptoethanol 0.01M) and rinsed thoroughly. The livers are minced in cold buffer (2.0 ml/g) and homogenized using a Potter-Elvejhem homogenizer. The homogenate is centrifuged at 5,000×g, 10 minutes (4° C.), and the supernatant poured through 2 layers of cheese cloth. The supernatant is then centrifuged at 15,000×g for 15 minutes (4°). Again the supernatant is filtered through 2 layers of cheese cloth, and centrifuged a third time at 100,000×g for 1.0 hour at 4° C. Following centrifugation the microsomal pellet is resuspended in a volume of buffer equivalent to 1/5 the volume of the original homogenate, and homogenized in a ground glass homogenizer.

Aliquotted microsomes are frozen at −80° C., and retain activity for at least two months.

Enzyme Assay

Reaction Mixtures are prepared in 50 ml round bottom pyrex glass tubes with tight-fitting, teflon-lined, screw caps. Tubes are cooled to 4° C., and the following components are added in sequence:

| | |
|---|---|
| 1. Potassium phosphate buffer (0.275 M, pH 7.4) | 0.36 ml |
| 2. KF (55 mM) | 0.36 ml |
| 3. NADPH (5.0 mM, freshly prepared) | 0.36 ml |
| 4. H$_2$O (or H$_2$O + test compound) | 0.16 ml |
| 5. MgCl$_2$ (27.5 mM) | 0.36 ml |
| 6. Microsomal Enzyme (0.48 mg microsomal protein in homogenization buffer) (15 μl prep.) 4/23/86 | 0.20 ml |
| | 1.8 ml |

This mixture is equilibrated under N$_2$ at 4° C. for 5–15 minutes. Reaction mixtures are then warmed to 30° C., and the enzyme reaction initiated by adding 0.2 ml of farnesyl pyrophosphate (219 μM) prepared in H$_2$O. Each tube is again overlayered with N$_2$, and incubated at 30° C. for 60 minutes. The reaction is stopped by the addition of 1.0 ml KOH (40%). Ethanol (95%) (spectral grade) (1.0 ml) is added to each tube. Docosane (5 nmoles in hexane) is added to each tube as an internal standard. The mixture is saponified at 65° C. for 30 minutes. The tubes are cooled to room temperature and extracted twice with 10.0 ml spectral grade hexane.

The upper organic phase fractions are pooled in glass 20.0 ml scintillation vials and reduced in volume to ≈1.0 ml under a stream of N$_2$. The sample is then transferred to acid-washed, conical bottom, glass (1.0 ml) microvials, and brought to dryness under N$_2$. The residue is resuspended in 50 μl hexane (spectral grade), and these samples are spun at 1000 rpm at room temperature for 10 minutes. Following centrifugation approximately 40 μl of supernatant is transferred to 100 μl acid-washed microvials with septa/crimp-top caps (compatible with the Hewlett-Packard GC auto injector).

Gas Chromatography

Two μL of each sample is injected onto a fused silica megabore DB-17 column (15M×0.525 mm) (J&W Scientific) using a splitless mode of injection. Gas flow rates are listed below:

| | |
|---|---|
| Make up gas (helium) | 20 ml/min. |
| Air | 400 ml/min. |
| Hydrogen | 30 ml/min. |
| Carrier (helium) | 15 ml/min. |
| Septum purge vent | 5 ml/min. (Septum purge off 0.00 min., on at 0.5 min.) |

The injector temperature is 200° C., and the FID detector temperature is set at 270° C. Oven temperature is programmed through a two ramp sequence as follows:

| Oven: |
|---|
| Initial temperature 180° C., initial time 10 minutes |
| Ramp one: 20° C./minute |
| Second temperature 250° C., second time 10 minutes |
| Ramp two: 20° C./minute |
| Third temperature 260° C., third time 10 minutes |
| (Equilibration time 1.0 minute) |

Using this gas chromatographic system, docasane (internal standard) has a retention time of 3.6–3.7 minutes, and squalene has a retention time of 14.7–14.9 minutes. The amount of squalene in each reaction mixture is determined by obtaining the areas under the squalene and docasane peaks and using the following formula to calculate the amount of squalene (nmoles) in the total reaction mixture.

Squalene (nmoles/reaction mixture) =

$$5.0 \text{ (nmoles docasane internal standard)} \times \frac{\text{Squalene Peak Area}}{\text{Docasane Peak Area}} \times RR*$$

*RR = Response Ratio [Docasane/Squalene]
*RR = 0.56

Compounds Testing

Compounds are dissolved in H$_2$O and added to reaction mixtures prior to addition of farnesyl pyrophosphate substrate. All reaction mixtures are run in duplicate, at several concentrations. Additionally, all compound I$_{50}$ values are derived from composite dose response data.

A pharmaceutical composition formed of at least one of the compounds of Formulae III, IV or VI in association with a pharmaceutical vehicle or diluent can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectable preparation is produced by asceptically placing 250 mg of sterile active ingredient into a vial, asceptically freeze-drying and sealing. For use, the contents of the vial are mixed with 2 ml of physiological saline, to produce an injectible preparation.

Introduction to Experimental

All temperatures are reported in degrees Centigrade.

$^1$H and $^{13}$C chemical shifts are reported as δ-values with respect to Me$_4$Si (δ=0). Coupling constants J are reported in Hz. Chemical ionization mass spectra (CI-MS) were determined with a Finnigan TSQ-4600 instrument equipped with a direct exposure probe using the indicated reagent gases. Fast atom bombardment mass spectra (FAB-MS) were recorded on a VG Analytical ZAB-2F spectrometer. Ions were sputtered (8 keV Xe)

from a matrix containing dithiothreitol, dithioerythritol, DMSO, glycerol and water.

TLC was performed on E. Merck Silica Gel 60 F-254 plates (0.25 mm) or E. Merck Cellulose F plates (0.1 mm). Flash chromatography was carried out using E. Merck Kieselgel 60 (230–400 mesh).

Reverse-phase chromatographic purification of salts or mixed ester-salts was carried on CHP20P gel or SP207SS gel, highly porous, polystyrenedivinyl benzene copolymers available from Mitsubishi Chemical Industries. The indicated general procedure was followed: An FMI Model RP-SY pump was utilized for solvent delivery. A column of CHP20P (2.5 cm diameter, 12-22 cm height) was slurry packed and washed with water (500–1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300-500 mL of the organic solvent, or an aqueous-organic mixture, just beneath the surface of a reservoir containing 300-500 mL of pure water. To start the gradient, the stopcock of the separatory funnel was opened, so that as the solvent was withdrawn by the pump from the reservoir, it was replaced with the solvent from the separatory funnel. HPLC-grade solvents were employed. Fractions were collected (10-15 mL each) at a flow rate of 5-10 mL per minute. Those fractions that contained pure product as judged by TLC or HPLC were pooled, the organic solvents were evaporated and the aqueous residue was lyophilized to dryness.

The following Examples represent preferred embodiments of the present invention.

EXAMPLE 1

(E)-[4-(2'-Methyl[1,1'-biphenyl]-4-yl)butenylidene]-bisphosphonic acid, tetrapotassium salt

A. 4-Bromo-2'-methyl-1,1'-biphenyl

A stirred solution of 21.0 mL of (2-methylphenyl)-magnesium bromide (42.0 mmol, 2.0M in diethyl ether) was evaporated in situ at room temperature. The syrupy residue was redissolved in 50 mL of THF and cooled to −20° C. under argon. To this solution was added a solution of 6.84 g (50.0 mmol) of thrice-fused zinc chloride in 50 mL of tetrahydrofuran (THF). The resulting thick white slurry was warmed to room temperature and stirred for 1 hour. After cooling to −78° C., a solution of 11.32 g (40.0 mmol) 1-bromo-4-iodobenzene and 500 mg (0.4 mmol) of tetrakis(triphenylphosphine)-palladium in 50 mL of THF was added over the course of thirty minutes. After an additional 20 minutes, the cooling bath was removed, the reaction stirred at room temperature for 2 hours and then quenched with 100 mL of 1M hydrochloric acid. The mixture was extracted twice with hexanes, the extracts combined, washed once with saturated sodium bicarbonate solution and once with 10% sodium thiosulfate. The organic extract was dried (MgSo$_4$) and evaporated. The crude product (11.3 g) was purified by distillation (bp 93°–95° C. at 0.5 Torr) to give 8.06 g (82%) of title compound as a colorless oil.

TLC Silica gel (hexanes) R$_f$=0.4.

IR (film) 3160, 3120, 2950, 2920, 2860, 1465, 1380, 1065, 995, 825, 755, 720 cm$^{-1}$.

$^1$H NMR (CDCl$_3$, 270 MHz) 7.51 (d, 2H, J=8.2 Hz), 7.20 (m, 6H), 2.24 (s, 3H) ppm.

MS (CI-NH$_3$, +ions) m/e 246, 248 (M).

B. (E)-3-(2'-Methyl[1,1'-biphenyl]-4-yl)-2-propenoic acid, butyl ester

A stirred solution of 6.00 g (24.3 mmol) of Part A compound, 106 mg (0.35 mmol) of tri-p-tolyl-phosphine, 4.4 mL (30.7 mmol) of n-butyl acrylate, 12 mL (50.0 mmol) of tributylamine and 10 mg (0.1 mmol) of hydroquinone was purged with a stream of nitrogen gas for 20 minutes at room temperature. To this mixture was added 4 mg (0.018 mmol) of palladium acetate. The reaction was heated to 150° C. for 18 hours under argon and then cooled to room temperature. The resulting slurry was diluted with ether, extracted twice with 50 mL of 1M hydrochloric acid, once with brine and once with saturated sodium bicarbonate solution. The organic phase was dried (MgSO$_4$) and evaporated. The crude product (7.5 g) was purified by flash chromatography on silica gel (5×25 cm column) eluted with 1 L of hexanes and then 1:1 dichloromethane/hexanes to give 5.68 g (79%) of title compound as a colorless oil.

TLC Silica gel (1:1 dichloromethane/hexanes) R$_f$=0.2.

IR (film) 3060, 3020, 2950, 2920, 2860, 1695, 1625, 1595, 1470, 1440, 1300, 1255, 1195, 1160, 825, 760 cm$^{-1}$.

$^1$H NMR (CDCl$_3$, 270 MHz) δ 7.73 (d, 1H, J=15.9 Hz), 7.56 (d, 2H, J=8.2 Hz), 7.30 (d, 2H, J=8.2 Hz), 7.20 (m, 4H), 6.47 (d, 1H, J=15.8 Hz), 4.23 (q, 2H, J=7.0 Hz), 2.27 (s, 3H), 1.70 (quintet, 2H, J=6.4 Hz), 1.43 (sextet, 2H, J=7.0 Hz), 0.97 (t, 3H, J=7.6 Hz) ppm.

MS (CI-NH$_3$, +ions) m/e 295 (M+H).

C. (E)-1-Acetoxy-3-[(2'-methyl[1,1'-biphenyl]-4-yl)]-2-propene

To a stirred solution of 4.47 g (15.2 mmol) of Part B compound in 50 mL of dichloromethane at 0° C. under nitrogen was added a solution of 32 mL (32 mmol, 1M in hexanes) of diisobutylaluminum hydride over 5 minutes. The resulting pale yellow solution was stirred for 2 hours and then quenched with 2 mL of methanol. The solution was then treated with 150 mL of 1M potassium sodium tartrate. A gel formed which dissolved within 5 minutes. The reaction mixture was extracted twice with ether. The extracts were combined, dried (Na$_2$SO$_4$) and evaporated. The resulting oil (3.6 g) was dissolved in 25 mL of THF, cooled to 0° C. under nitrogen and 4.6 mL (25 mmol) of diisopropylethylamine and 2.4 mL (25 mmol) of acetic anhydride were added. After 1 hour, the reaction mixture was diluted with ether, washed twice with 1M hydrochloric acid, once with brine and once with saturated sodium bicarbonate. The organic phase was dried (MgSO$_4$) and evaporated onto 10 g of silica gel. Purification by flash chromatography on silica gel (5×20 cm column) eluted with 3:2 dichloromethane:hexane to give title compound as a white solid, m.p. 54°-56° C., 3.55 g, 88% from Part B compound.

TLC Silica gel (3:2 dichloromethane/hexanes) R$_f$=0.2.

$^1$H NMR (CDCl$_3$, 270 MHz) δ 7.43 (d, 2H, J=8.2 Hz), 7.20 (m, 6H), 6.70 (d, 1H, J=15.8 Hz), 6.32 (dt, 1H, J=15.8, 6.4 Hz), 4.74 (dd, 2H, J=1.1, 6.4 Hz), 2.27 (s, 3H), 2.11 (s, 3H) ppm.

MS (CI-NH$_3$, +ions) m/e 267 (M+H).

Anal. Calc'd for $C_{18}H_{18}O_2$: C, 81.17; H, 6.81; Found: C, 80.87; H, 6.82.

D.

(E)-[4-(2'-Methyl[1,1'-biphenyl]-4-yl)-butenylidene]bisphosphonic acid, tetraethyl ester To a stirred solution of 2.036 g (7.64 mmol), of Part C compound, 3.81 mL (15.4 mmol, 2.0 equivalents) of bis(trimethylsilyl)acetamide, 4.39 g (15.2 mmol, 2.0 equivalents) of tetraethyl methylenediphosphonate and 110 mg (0.42 mmol) of triphenylphosphine in 25 mL of THF under argon was added 250 mg (0.22 mmol) of tetrakis(triphenylphosphine)palladium. The resulting mixture was heated to reflux for 24 hours. The reaction was cooled and evaporated and pumped at room temperature at 0.2 Torr for 24 hours. The residue was diluted with dichloromethane and evaporated onto 15 g of silica gel. Purification by flash chromatography on silica gel (5×20 cm column) eluted with 1:4 isopropanol/hexanes gave title compound as a colorless oil, 3.31 g, 87% yield.

TLC Silica gel (1:4 isopropanol/hexanes) $R_f = 0.2$.

IR (film) 2980, 2840, 2820, 1470, 1430, 1380, 1240, 1155, 1090, 1020, 960, 850, 780, 760 cm$^{-1}$.

$^1$H NMR (CDCl$_3$, 270 MHz) δ 7.40 (d, 2H, J=8.2 Hz), 7.20 (m, 6H), 6.53 (d, 1H, J=15.8 Hz), 6.42 (dt, 1H, J=15.8, 5.8 Hz), 4.20 (m, 8H), 2.89 (tt, 2H, J=6.4, 16.8 Hz), 2.49 (tt, 1H, J=6.4, 23.6 Hz), 2.27 (s, 3H), 1.35 (dt, 12H, J=1.8, 5.8 Hz) ppm.

MS (CI-NH$_3$, +ions) m/e 495 (M+H).

E.

(E)-[4-(2'-Methyl[1,1'-biphenyl]-4-yl)-butenylidene]bisphosphonic acid, tetrapotassium salt To a stirred solution of 1.45 g (2.94 mmol) of Part D compound in 15 mL of dichloromethane at room temperature under nitrogen was added 1.24 mL (9.0 mmol, 3.0 equivalents) of 2,4,6-collidine and then 2.46 mL (18.0 mmol, 6.0 equivalents) of bromotrimethylsilane. The clear, colorless solution was stirred for 24 hours and then evaporated at room temperature. The residue was treated with 18 mL (18.0 mmol, 6.0 equivalents) of 1.0M potassium hydroxide solution, diluted with water and lyophilized. The lyophilate was purified by MPLC (2.5×15 cm column, SP207SS Sepabeads, water as elutent). The chromatography afforded pure fractions which were pooled, filtered and precipitated with acetone to give the title compound 575 mg (33%) of a white solid. Slightly impure fractions were lyophilized to give an additional 630 mg (35%) of title compound.

IR (KBr pellet) 3427, 3021, 2953, 2922, 1633, 1157, 1128, 1107, 1088, 1005, 970, 758 cm$^{-1}$.

$^1$H NMR (D$_2$O, 270 MHz) δ 7.53 (d, 2H, J=8.2 Hz), 7.30 (m, 6H), 6.59 (m, 2H), 2.72 (tt, 2H, J=5.8, 7.0 Hz, 2.23 (s, 3H), 1.93 (tt, 1H, J=7.0, 21.1 Hz) ppm.

MS (FAB, +ions) m/e 535 (M+H), 497 (M-K+2H), 479 (M-K+2H-H$_2$O), 459 (M-2K+3H).

Anal. Calc'd for $C_{17}H_{16}K_4PO_6 \cdot 1.85H_2O$: C, 35.95; H, 3.50; P, 10.91; Found: C, 36,26; H, 3.89; P, 11.27.

Following the procedure of Example 1 substituting the allylic ester in Column I of the table set out below in place of the Example 1 Part C allylic ester, the product and yields obtained as shown in Columns II and III are obtained.

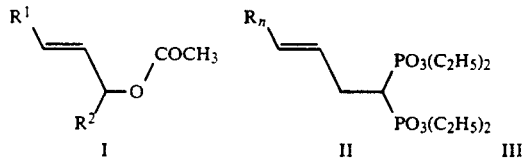

| Ex. No. | R$^1$ | R$^2$ | Product R$_n$ | Yield % |
|---|---|---|---|---|
| 2 | phenyl | H | phenyl | 85 |
| 3 | H | H | H | 62 |
| 4 | 2-methylbiphenyl | H | 2-methylbiphenyl | 81 |
| 5 | 2'-methylbiphenyl | H | 2'-methylbiphenyl | 87 |
| 6 | 4-(C$_6$H$_5$CH$_2$)phenyl | H | 4-(C$_6$H$_5$CH$_2$)phenyl | 57 |

-continued

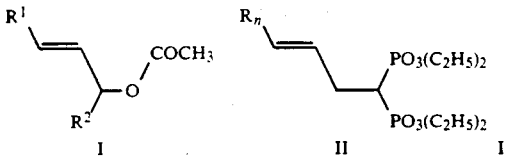

| Ex. No. | R¹ | R² | Product R_n | Yield % |
|---|---|---|---|---|
| 7 | F-C₆H₄-C₆H₄- | H | F-C₆H₄-C₆H₄- | 62 |
| 8 | CH₃O-C₆H₄-C₆H₄- | H | CH₃O-C₆H₄-C₆H₄- | 62 |

EXAMPLE 2

(E)-[4-([1,1'-Biphenyl]-4-yl)-3-butenylidene]bisphosphonic acid, tetraethyl ester

A. α-Ethenyl[1,1'-biphenyl]-4-methanol acetate

To a stirred solution of 22.0 mL (22 mmol, 1M in THF) of vinylmagnesium bromide solution cooled to −22° C. under nitrogen was added a solution of 3.64 g (20.0 mmol) of ([1,1'-biphenyl]-4-yl)-carboxaldehyde in 20 mL of THF over 10 minutes. The resulting yellow solution was allowed to warm to room temperature in situ and after 16 hours, the reaction mixture was cooled to 0°–5° C. and 2.4 mL (25 mmol) of acetic anhydride was added. After 10 minutes, the reaction was poured into 50 mL of saturated sodium bicarbonate solution and extracted twice with ether. The ether extracts were combined, dried (MgSO₄) and evaporated. Purification by flash chromatography on silica gel (5×25 cm column) using 35:65 dichloromethane/hexanes as elutent gave 3.07 g, 61%, of title compound as a light yellow solid, mp 39°–41° C.

TLC Silica gel (35:65 dichloromethane/hexanes) $R_f$=0.21.

IR (film) 3095, 3020, 2990, 1730, 1410, 1370, 830, 765 cm⁻¹.

¹H NMR (CDCl₃, 270 MHz) δ 7.57 (m, 4H), 7.42. (d, 2H, J=6.8 Hz), 7.40 (m, 2H), 7.34 (m, 1H), 6.31 (d, 1H, J=6 Hz), 6.03 (ddd, 1H, J=6.0, 10.3, 17.1 Hz), 5.28 (m, 2H), 2.11 (s, 3H) ppm.

MS (CI-NH₃, +ions) m/e 252 (M).

B.
(E)-[4-([1,1'-Biphenyl]-4-yl)-3-butenyl-idene]bisphosphonic acid, tetraethyl ester To a stirred solution of 505 mg (2.0 mmol) of Part A compound, 1.0 mL (4.0 mmol) of bis(trimethylsilyl)acetamide, 1.15 g (4.0 mmol) of tetraethyl methylenediphosphonate, and 105 mg (0.4 mmol) of triphenyl phosphine in 5 mL of THF at room temperature under nitrogen was added 225 mg (0.2 mmol) of tetrakis(triphenylphosphine)palladium. The reaction mixture was heated to reflux for 16 hours. After cooling to room temperature, the mixture was diluted with ether, washed once with 1M HCl, once with water and once with saturated sodium bicarbonate. The organic extract was dried (MgSO₄) and evaporated to give an orange oil. Purification by flash chromatography on silica gel (5×15 cm column) using 18:82 isopropyl alcohol/hexanes as elutent gave 790 mg (82%) of title compound as a light yellow oil.

TLC Silica gel (18:82 isopropyl alcohol/hexanes) $R_f$=0.17.

IR (film) 3020, 2990, 1255, 1020, 970 cm⁻¹.

¹H NMR (CDCl₃, 270 MHz) δ 7.59 (d, 2H, J=7.4 Hz), 7.53 (d, 2H, J=8.1 Hz), 7.42 (m, ' '=6.0 Hz), 7.34 (m, 1H), 6.52 (d, 1H, J=5.8 Hz) 1 (dt, 1H, J=6.8, 5.8 Hz), 4.20 (m, 8H), 2.89 (tt, 2) ;=6.0, 17.1 Hz), 2.49 (tt, 2H, J=6.0, 24 Hz), 1.34 (dt, 12H, J=2.5, 7.3 Hz) ppm.

MS (CI-NH₃, +ions) m/e 481 (M+H).

The above ester compounds prepared by the method of the invention may be converted to their corresponding alkali metal salts by treatment with iodotrimethylsilane (TMSI) or bromotrimethylsilane (TMSBr), optionally in the presence of a proton scavenger, such as 2,4,6-collidine or bis(trimethylsilyl)trifluoroacetamide followed by hydrolysis with metal hydroxides; or to the free acids by treatment with TMSI or TMSBr as above, followed by treatment with water or alcohol, and as such may be used as squalene synthetase inhibitors to inhibit cholesterol biosynthesis.

What is claimed is:

1. A process for preparing a 3-alkenylidene-1,1-bisphosphonate, which comprises reacting an allylic ester of the structure

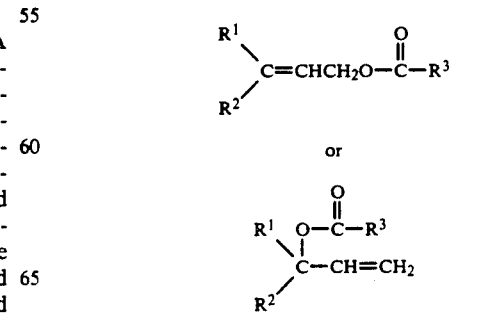

and a methylene bisphosphonate of the structure

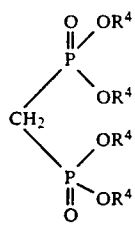

in the presence of a palladium catalyst to form a 3-alkenylidene-1,1-bisphosphonate of the structure

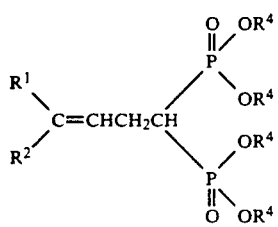

where in the above structures $R^1$ and $R^2$ are the same or different and are H, alkyl, aryl or vinyl;

$R^3$ is alkyl, aryl, alkoxy or aryloxy; and $R^4$ is alkyl.

2. The process as defined in claim 1 wherein the palladium catalyst is tetrakis(triphenyl phosphine) palladium.

3. The process as defined in claim 1 wherein the reaction is carried out in the presence of a phosphine ligand.

4. The process as defined in claim 2 wherein the ligand is triphenyl phosphine.

5. The process as defined in claim 1 wherein the reaction is carried out in the presence of a proton scavenger.

6. The process as defined in claim 4 wherein the proton scavenger is bis(trimethylsilyl)acetamide.

7. The process as defined in claim 4 wherein the allylic ester starting material has the structure

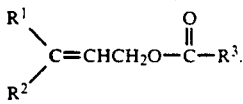

8. The process as defined in claim 6 wherein the allylic ester starting material has the structure

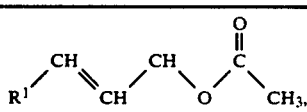

| $R^1$ | |
|---|---|
| 1. | 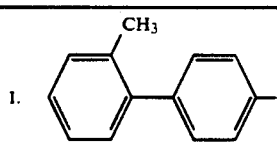 |
| 2 |  |
| 3 | H |

-continued

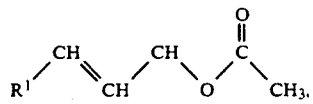

| $R^1$ | |
|---|---|
| 4 |  |
| 5 | 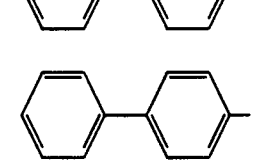 |
| 6 | 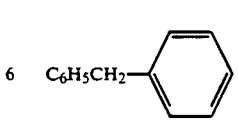 |
| 7 | 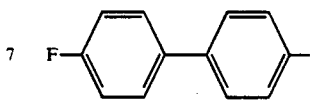 |
| 8 | 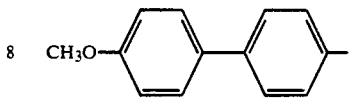 | or has the structure

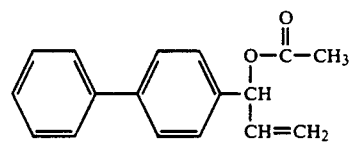

9. The process as defined in claim 8 further including the step of hydrolyzing the bisphosphonate ester to the corresponding metal salt.

10. The process as defined in claim 1 wherein the bisphosphonate starting material is employed in a molar ratio to the allylic ester starting material of within the range of from about 1:1 to about 5:1.

11. The process as defined in claim 1 wherein the reaction is carried out at a temperature of within the range of from about 25° C. to about 110° C. under an inert atmosphere.

12. The process as defined in claim 1 wherein the dialkylated bisphosphonate of the structure

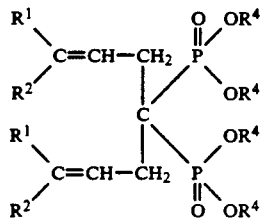

is also formed.

13. The process as defined in claim 1 wherein the proton scavenger bis(trimethylsilyl)-acetamide is employed and the resulting reaction product is primarily the monoalkylated bisphosphonate.

14. The process as defined in claim 13 wherein a base is employed and the resulting reaction product is primarily the dialkylated bisphosphonate.

15. A process for preparing a bisphosphonate of the structure

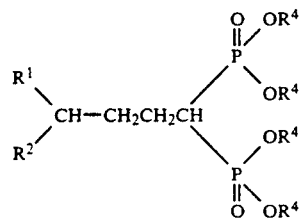

which comprises reacting an allylic ester of the structure

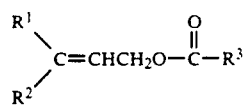

or

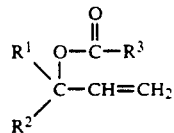

and a methylene disphosphonate of the structure

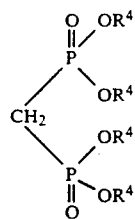

in the presence of a palladium catalyst to form a 3-alkenylidene-1,1-bisphosphonate of the structure

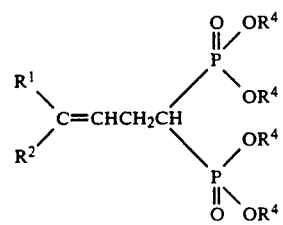

where in the above structures $R^1$ and $R^2$ are the same of different and are H, alkyl, aryl or vinyl;

$R^3$ is alkyl, aryl, alkoxy or aryloxy; and $R^4$ is alkyl, and hydrogenating the 3-alkenylidene-1,1-bisphosphonate to form the corresponding saturated analog.

16. The process as defined in claim 15 wherein the palladium catalyst is tetrakis(triphenyl phosphine)palladium.

17. The process as defined in claim 15 wherein the hydrogenation is carried out employing a Pd/C catalyst.

* * * * *